Figure 1:
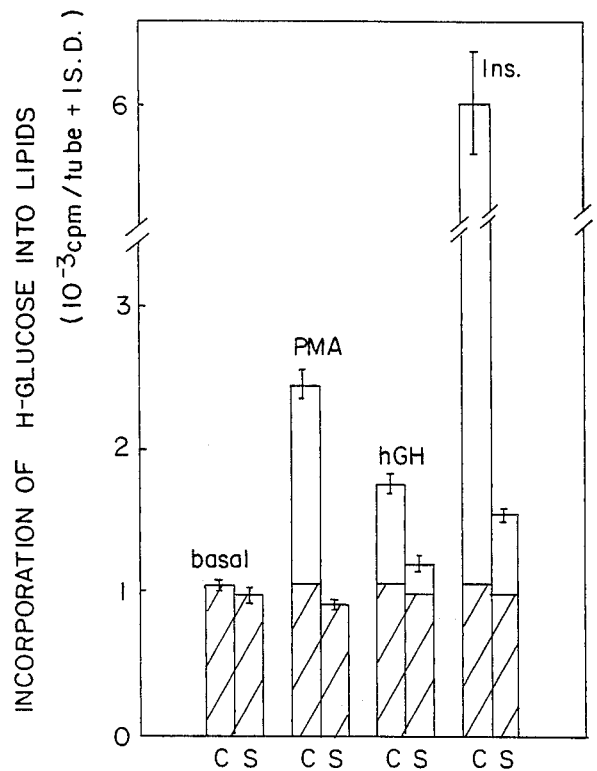

United States Patent [19]

DeMeyts et al.

[11] Patent Number: 4,952,567
[45] Date of Patent: Aug. 28, 1990

[54] INHIBITION OF LIPOGENESIS

[75] Inventors: Pierre DeMeyts; Jean Smal, both of Pasadena; Yoko Fujita-Yamaguchi, Glendora, all of Calif.

[73] Assignee: City of Hope, Duarte, Calif.

[21] Appl. No.: 216,379

[22] Filed: Jul. 8, 1988

Related U.S. Application Data

[63] Continuation-in-part of Ser. No. 191,986, May 9, 1988, abandoned.

[51] Int. Cl.$^5$ .................. A61K 31/70; A61K 31/715; A61K 31/73
[52] U.S. Cl. ...................................... 514/54; 514/211; 514/669; 514/25; 514/909; 536/17.9; 536/18.7; 536/54.0; 536/55.0; 536/55.1
[58] Field of Search .................. 514/54, 211, 669, 25, 514/909; 536/17.9, 18.7, 54.0, 55.0, 55.1

[56] References Cited

U.S. PATENT DOCUMENTS

| | | | |
|---|---|---|---|
| 4,004,030 | 1/1977 | Schwarzmann et al. | 514/669 |
| 4,476,119 | 10/1984 | della Valle et al. | 514/54 |
| 4,593,091 | 6/1986 | della Valle et al. | 514/54 |
| 4,731,210 | 3/1988 | Weder et al. | 264/4.6 |
| 4,735,939 | 4/1988 | McCoy et al. | 514/211 |

OTHER PUBLICATIONS

Moody et al., *Horm. Metab. Res.*, 1974, vol. 6, pp. 12–16.
Gliemann et al., *Diabetologia*, 1974, vol. 10, pp. 105–113.
Freychet et al., *Diabetologia*, 1974, vol. 10, pp. 1–5.
Keefer et al., *Proc. Natl. Acad. Sci.*, 1981, vol. 78(3), pp. 1391–1395.

*Primary Examiner*—2
*Assistant Examiner*—Ronald W. Griffin
*Attorney, Agent, or Firm*—Edward S. Irons

[57] ABSTRACT

A process which comprises administering an antagonist of protein kinase C and/or the insulin receptor tyrosine kinase to a mammal in an amount therapeutically effective to inhibit lipogenesis in the mammal.

20 Claims, 3 Drawing Sheets

INHIBITION OF LIPOGENESIS

This application is a continuation-in-part of application Ser. No. 191,986 filed May 9, 1988, now abandoned.

This invention relates to the inhibition and the complete suppression of lipogenesis. More particularly, the invention relates to the treatment and prevention of obesity in mammals, including humans, by the administration of a protein kinase antagonist, including an antagonist of protein kinase C and/or of the insulin receptor tyrosine kinase, preferably a sphingolipid, a lysosphingolipid, an aminoacridine, staurosporine and therapeutically effective derivatives thereof.

DESCRIPTION OF THE INVENTION

The excessive accumulation of lipids in fat cells is one of the major features of human and animal obesity. Lipogenesis is stimulated by insulin. The effects of insulin are thought to involve the activation of cellular protein kinases. Two of the best studied kinases are the insulin receptor tyrosine kinase and protein kinase C. Pursuant to the preferred embodiment of this invention mammalian obesity is treated by administering a protein kinase C antagonist or an insulin receptor tyrosine kinase antagonist in an amount therapeutically effective to block or completely suppress fat cell lipogenesis. Application Ser. No. 135,073 filed Dec. 18, 1987, now abandoned, describes one embodiment of the invention pursuant to which a member of a family of complex lipids known to the art as sphingolipids and (lyso)sphingolipids is administered to mammals, including humans, to block or to completely suppress fat cell lipogenesis, and thus to treat or prevent mammal obesity.

Sphingolipids comprise a large group of long chain bases with a common 2 amino-1,3 diol system and constitute one of two main classes of complex lipids that participate in the lipid phase and surface structure of biological membranes. The sphingolipids include subgroups of divergent molecular structure such as ceramide, sphingomyelin, galacto-and glucocerebrosides, sulfatides, the neutral glycosphingolipids, the acidic gangliosides and the (lyso)sphingolipids in which the 2-amino group is unsubstituted.

Formula I includes some of the lysosphingolipids useful in the invention:

$$CH_3(CH_2)_{12}CH=CH-\underset{OH}{CH}-\underset{NH_2}{CH}-CH_2O-X \qquad I$$

wherein X may be, e.g., H (sphingosine) galactose (psychosine)

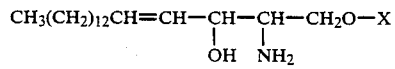

Gal—Gal NAc\
            \Gal—Glc— (lyso GM$_1$)\
            /\
      Sia

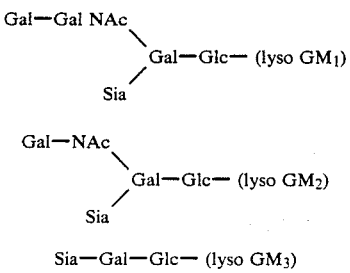

Sia—Gal—Glc— (lyso GM$_3$)

and derivatives thereof.

The preferred compound for use in this embodiment of the invention is sphingosine.

Application Ser. No. 191,986 filed May 9, 1988 teaches that the compound staurosporine, which is an antagonist of both protein kinase C and of the insulin receptor tyrosine kinase, is also a potent inhibitor of lipogenesis. Staurosporine is a microbial alkaloid recently found to be a protein kinase inhibitor having the formula II:

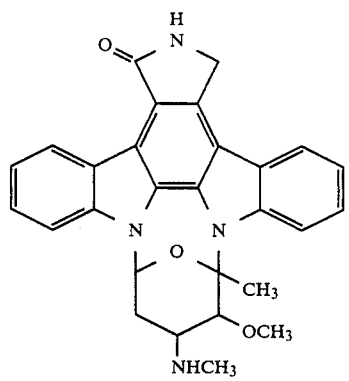

Staurosporine

It is available from Kyowa Hakko Kogyo Co., Tokyo, Japan.

Aminoacridine constitutes an additional group of kinase C inhibitors useful in the practice of this invention. The aminoacridine are described in Hannun and Bell, Aminoacridine, Potent Inhibitors of Protein Kinase C, *J. Biol. Chem.* 283:5124–5131 (1988). This embodiment of the invention specifically includes, among other aminoacridines, the compounds shown by Hannun and Bell to be protein kinase C inhibitors. Acridine orange is preferred and has been shown to block both basal and insulin-stimulated lipogenesis in rat adipocytes. Inhibition is maximum at 10 $\mu$M.

EXEMPLIFICATION OF THE INVENTION

This invention involves the discovery that protein kinase antagonists, preferably sphingolipids and (lyso)sphingolipids or staurosporine inhibit or completely suppress lipogenesis in the fat cells of mammals. The degree of inhibition is a function of the effective amount of protein kinase antagonist, e.g., sphingolipid or (lyso)sphingolipid or staurosporine in or available to the fat cells. More particularly, it has been discovered that the stimulation of fat cell lipogenesis by insulin, growth hormone and phorbol esters is blocked reversibly by the action of a protein kinase antagonist such as staurosporine or a lipid useful in this invention at an effective but relatively lower concentration, whereas at higher concentrations basal lipogenesis (lipogenesis in the absence of hormones) is completely suppressed.

FIG. 1 illustrates the effect of sphingosine on the maximal stimulation of lipogenesis in rat adipocytes by phorbol ester (PMA), human growth hormone (hGH) and insulin (INS).

The incorporation of the tracer D-3[$^3$H]-glucose into lipids is expressed in counts per minute of radioactivity (=cpm) per tube. It is the mean of a triplicate measurement, plus or minus one standard deviation (1 S.D.). The values obtained have been divided by 1,000 for simplifying the graph (=X 10$^{-3}$). Thus, a value of 3 on the FIG. I graph means that 3,000 cpm were actually measured.

Cells were incubated without hormone (basal--black bars) or with respectively 1000 ng/ml PMA, 1000 ng/ml hGH or 100 ng/ml insulin in the absence (bars c) or in the presence (bars s) of 50 μM of sphingosine (combined black and white bars).

At 100 μM sphingosine both basal and hormone stimulated lipogenesis are reduced to zero.

The lipogenesis assay has been conducted according to Smal, et al. *J. Biol. Chem.* 262:11071–11079 (1987). Briefly, dissected epididymal and retroperitoneal fat pads were digested under vigorous shaking at 37° C. for 30 min with collagenase (1.0 mg/ml) in Krebs-Ringer-Hepes (KRH) buffer, pH 7.4, 35 mg/ml dialyzed bovine serum albumine (BSA), 0.27 mM glucose. After filtration on cheesecloth and 4 washes in KRH with 10 mg/ml BSA, the adipocytes were preincubated for 4 hours at 37° C. in the same buffer. Sphingosine (100 mM stock solution in ethanol) was added to the cells (final concentration:50 μM) 10 min before the lipogenesis assay. The same concentration of ethanol, without sphingosine, was added to the control cells.

The lipogenesis assay was performed in triplicate in 6 ml polyethylene vials by adding successively 400 μl of adipocyte suspension ($80 \times 10^3$ cells/ml), 50 μl of KRH buffer pH 7.4 (1% BSA, 0.27 mM glucose) without hormone (basal lipogenesis) or with human growth hormone (1000 ng/ml), insulin (100 ng/ml) or phorbol ester PMA (1000 ng/ml) and 50μl D-[3-$^3$H]-glucose in a total volume of 0.5 ml. The vials were incubated 2 hours at 37° C. under gentle shaking. The incubation was interrupted by adding 5 ml/tube of toluene scintillator (1 liter toluene+0.3 g of 1,4bis[2-(4-methyl-5phenyloxazolyl) benzene and 5 g of 2,5-diphenyloxazole under vigorous shaking (30s to break the cells) followed by a rest of at least 1 hour to allow extraction of lipids into the toluene phase before counting. The samples were counted in a Beckman LS 1880 beta counter. The counting efficiencies for the different samples were measured by internal standardization with quenched tritiated standards. The incorporation of D-[3-$^3$H]-glucose into lipids is expressed in cpm $\times 10^{-3}$/tube±1 standard deviation.

Figure 2A:
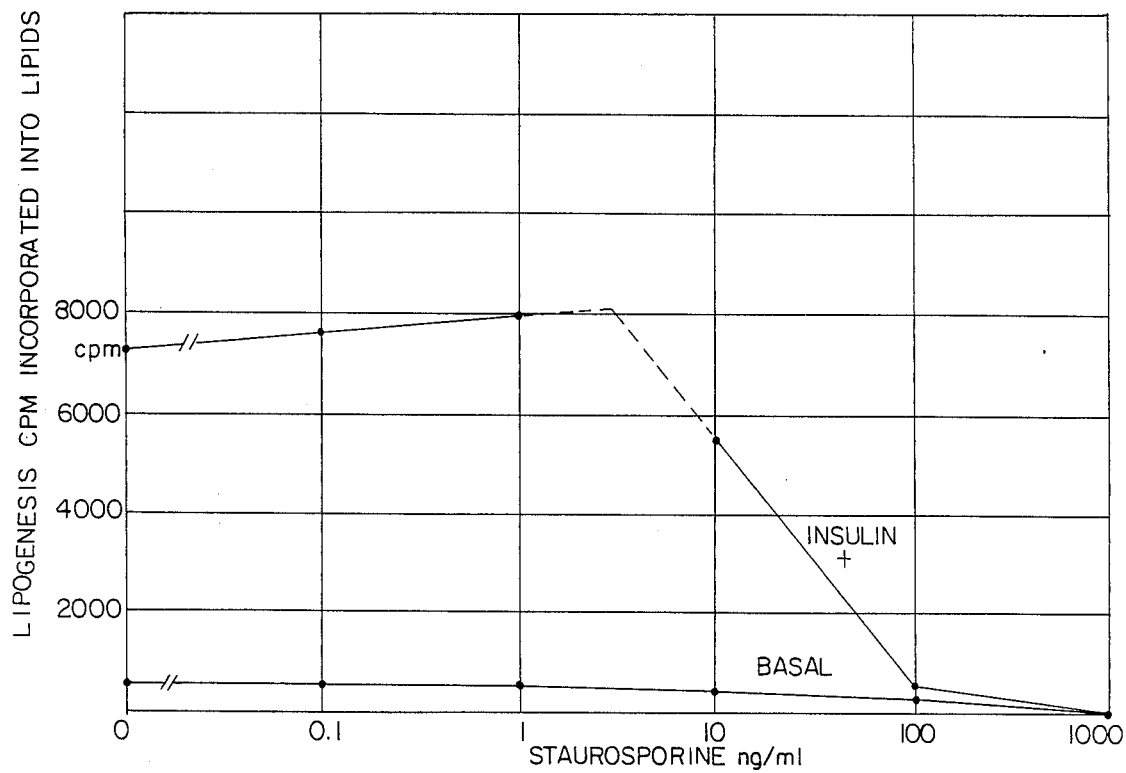
Figure 2B:
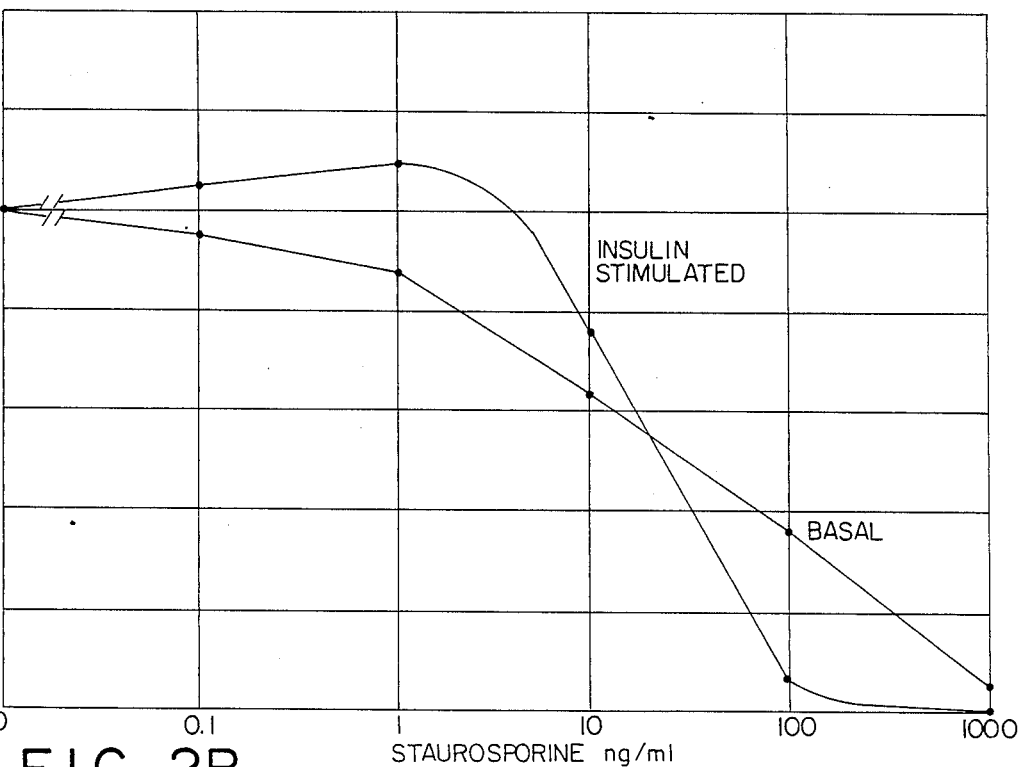

FIG. 2A illustrates the effect of staurosporine on the maximal stimulation of lipogenesis in isolated rat adipocytes by insulin. The incorporation of the tracer D-3[$^3$H]-glucose into lipids is expressed in counts per minute of radioactivity (=cpm) per tube. It is the mean of a triplicate measurement, plus or minus one standard derivation (1 S.D.). Cells were incubated without (basal curve) or with 100 ng/ml insulin (insulin curve) in the presence of increasing doses (0–21.4 μM) of staurosporine. Lipogenesis assays were conducted according to Smal, supra. In FIG. 2B, the results of the experiment shown on FIG. 2A are normalized: insulin-stimulated lipogenesis and basal lipogenesis in the presence of increasing doses of staurosporine are expressed in % of their initial values without staurosporine. Stimulated lipogenesis in rat adipocytes are progressively inhibited by staurosporine in a dose-dependent manner. Basal and insulin-stimulated lipogenesis are completely inhibited by staurosporine at about 2.5 micromolar and 25 micromolar respectively, whereas a 100 micromolar concentration of sphingosine is necessary to yield a comparable inhibitory effect.

Administration and Dosage

The selection of a mode of administration and of dosage level is within the competence and discretion of persons skilled in the art. The invention in its broader aspects includes a pharmaceutical composition containing a protein kinase antagonist, e.g., staurosporine or a sphingolipid or a lysosphingolipid useful to block lipid metabolism in mammals, including man. The antagonist may be administered per se or in combination with therapeutically acceptable adjuvants, e.g., liposomes.

The preferred (lyso)sphingolipid is sphingosine.

Parenteral administration is preferred. Percutaneous administration using gels or creams containing a permeabilizing agent such as dimethylsulfoxide may be used. The protein kinase antagonist, i.e., staurosporine or a sphingolipid or lysosphingolipid is administered in an amount therapeutically effective to partially or completely suppress the hormonal or basal stimulation of lipogenesis in mammalian fat cells.

The degree of suppression is a function of dosage level. Preferably about 15 to about 100 mg/kg of protein kinase antagonist is appropriate for sphingolipids. Administration of at least about 15 mg/kg is appropriate to partially suppress lipogenesis. Administration of at least about 60 mg/kg is indicated for the complete suppression of basal lipogenesis. For staurosporine at least about 15 mg/kg is indicated for complete suppression of basal lipogenesis. Administration may appropriately continue over an appropriate time period until the desired therapeutic effect is observed.

A number of drugs are known to interfere with lipogenesis, e.g., hormone (catecholamines, glucagon, ACTH) clofibrate, halogenate, fenfluramine, amphetamine, cinchocaine, chlorpromazine, and some derivatives thereof. None of these drugs suppress lipogenesis as effectively as the protein kinase antagonists of this invention.

We claim:

1. A method which comprises administering a protein kinase antagonist to a mammal in an amount therapeutically effective to inhibit lipogenesis in said mammal.

2. The method of claim 1 in which the protein kinase antagonist is a lysosphingolipid, an aminoacridine, or staurosporine.

3. The method of claim 2 in which the mammal is a human.

4. The method of claim 3 in which the protein kinase antagonist is staurosporine.

5. The method of claim 3 in which the protein kinase antagonist is administered in an amount therapeutically effective to block hormonal stimulation of lipogenesis in said human.

6. The method of claim 4 in which the protein kinase antagonist is administered in an amount therapeutically sufficient to suppress basal lipogenesis.

7. A method which comprises administering a sphingolipid or a (lyso)sphingolipid to a mammal in an amount therapeutically effective to inhibit lipogenesis in said mammal.

8. The method of claim 7 in which sphingosine is administered.

9. The method of claim 7 in which the mammal is a human.

10. The method of claim 9 in which the sphingolipid or (lyso)sphingolipid is administered in an amount sufficient to block the hormonal stimulation of lipogenesis in said human.

11. The method of claim 9 in which the sphingolipid or (lyso)sphingolipid is administered in an amount sufficient to suppress basal lipogenesis.

12. A method for the treatment of obesity in a mammal which comprises administering to said mammal a sphingolipid or a (lyso)sphingolipid in an amount therapeutically effective to block basal fat accumulation.

13. A method for the treatment of obesity in a mammal which comprises administering a (lyso)sphingolipid to said mammal in an amount therapeutically effective to block basal fat accumulation.

14. A method for the treatment of obesity in a mammal which comprises administering a (lyso)sphingolipid to said mammal in an amount therapeutically effective to block insulin stimulated fat accumulation.

15. The method of claims 13 or 14 in which the mammal is a human.

16. The method of claims 13 or 14 in which the lysosphingolipid is sphingosine.

17. The method which comprises administering an aminoacridine to a mammal in an amount therapeutically effective to inhibit lipogenesis in said mammal.

18. The method of claim 17 in which the mammal is a human and the aminoacridine is acridine orange.

19. The method of claim 17 in which the mammal is a human.

20. A method as defined by claim 17 or claim 18 in which said protein kinase antagonist is administered in an amount corresponding to about 15 mg/kg to about 100 mg/kg of body weight of said mammal.

* * * * *

UNITED STATES PATENT AND TRADEMARK OFFICE
CERTIFICATE OF CORRECTION

PATENT NO. : 4,952,567

DATED : August 28, 1990

INVENTOR(S) : Pierre De Meyts, Jean Smal, and Yoko Fujita-Yamaguchi

It is certified that error appears in the above-identified patent and that said Letters Patent is hereby corrected as shown below:

Column 1, line 4, after the title, insert:

--This invention was made with government support under Grant No. DK29970 awarded by the National Institutes of Health. The government has certain rights in the invention.--

Signed and Sealed this

Twenty-third Day of February, 1993

Attest:

STEPHEN G. KUNIN

Attesting Officer

Acting Commissioner of Patents and Trademarks

UNITED STATES PATENT AND TRADEMARK OFFICE
CERTIFICATE OF CORRECTION

PATENT NO. : 4,952,567

DATED : August 28, 1990

INVENTOR(S) : DeMeyts et al

It is certified that error appears in the above-identified patent and that said Letters Patent is hereby corrected as shown below:

Cover Page Column 1, Item [63] after "abandoned" insert:

--, which is a continuation-in-part of Ser.No. 135,073, December 18, 1987 abandoned.

Signed and Sealed this

Ninth Day of March, 1993

Attest:

STEPHEN G. KUNIN

Attesting Officer

Acting Commissioner of Patents and Trademarks